(12) United States Patent
Sun

(10) Patent No.: US 9,931,281 B2
(45) Date of Patent: Apr. 3, 2018

(54) MULTI-FUNCTIONAL SELF-HEALING DENTAL COMPOSITES, METHODS OF SYNTHESIS AND METHODS OF USE

(71) Applicant: ADA Foundation, Chicago, IL (US)

(72) Inventor: Jirun Sun, Rockville, MD (US)

(73) Assignee: ADA FOUNDATION, Chicago, IL (US)

( * ) Notice: Subject to any disclaimer, the term of this patent is extended or adjusted under 35 U.S.C. 154(b) by 30 days.

(21) Appl. No.: 14/952,492

(22) Filed: Nov. 25, 2015

(65) Prior Publication Data

US 2016/0193119 A1 Jul. 7, 2016

Related U.S. Application Data

(60) Provisional application No. 62/100,670, filed on Jan. 7, 2015.

(51) Int. Cl.
*A61K 6/083* (2006.01)
*A61K 6/00* (2006.01)

(52) U.S. Cl.
CPC ............ *A61K 6/083* (2013.01); *A61K 6/0052* (2013.01); *A61K 6/0091* (2013.01)

(58) Field of Classification Search
None
See application file for complete search history.

(56) References Cited

U.S. PATENT DOCUMENTS

| | | | | |
|---|---|---|---|---|
| 6,518,330 B2 * | 2/2003 | White | ............... | B29C 73/163 428/402.21 |
| 6,602,932 B2 * | 8/2003 | Feldheim | ............ | B01J 13/14 523/201 |
| 6,858,659 B2 * | 2/2005 | White | ............... | B29C 73/163 428/402 |
| 8,557,329 B2 * | 10/2013 | Dai | .................. | C23C 18/1212 427/127 |
| 8,735,463 B2 * | 5/2014 | Gross | ................. | A61K 6/083 433/228.1 |
| 2005/0037050 A1 * | 2/2005 | Weber | ................... | A61F 2/04 424/426 |

(Continued)

*Primary Examiner* — Peter A Salamon

(57) ABSTRACT

A multi-functional self-healing dental composite may intrinsically repair the micro-crack and prevent the crack from propagating to catastrophic failure, thus significantly extending the service life of the restorative material. The self-healing dental composite includes a dental resin matrix, fillers, healing powder, and healing liquid containing micro-capsules distributed throughout the matrix. Each of the micro-capsules have a silica she formed by the hydrolysis condensation of TEOS in the presence of an aqueous solution of a healing liquid. The healing liquid includes a homo-polymers(s) and/or copolymer(s) of carboxylic acid(s). The healing powder particles distributed throughout the resin matrix, and include alumina, silica and other elements. The self-healing may be triggered automatically as a result of micro-cracking, induced by thereto/mechanical fatigue. During the self-healing process, antibacterial agents may be released to provide protection of the composites against cariogenic bacteria. The self-healing dental composites also may improve tooth remineralization, and caries prevention though fluoride release.

19 Claims, 2 Drawing Sheets

(56) References Cited

U.S. PATENT DOCUMENTS

| | | | |
|---|---|---|---|
| 2008/0300340 A1* | 12/2008 | Gross | A61K 6/083 |
| | | | 523/120 |
| 2010/0272764 A1* | 10/2010 | Latta | A61K 8/11 |
| | | | 424/401 |
| 2011/0071234 A1* | 3/2011 | Gross | A61K 6/0055 |
| | | | 523/116 |
| 2013/0011453 A1* | 1/2013 | Latta | A61K 8/11 |
| | | | 424/401 |

* cited by examiner

MULTI-FUNCTIONAL SELF-HEALING DENTAL COMPOSITES, METHODS OF SYNTHESIS AND METHODS OF USE

RELATED APPLICATIONS

This application claims priority to U.S. Provisional Patent Application 62/100,670, filed Jan. 7, 2015 and entitled "MULTI-FUNCTIONAL SELF-HEALING DENTAL COMPOSITES, METHODS OF SYNTHESIS AND METHODS OF USE," the entire disclosure of which is hereby incorporated by reference.

BACKGROUND

Resin composites may be used in a variety of dental applications including as resin filler material for cavities. Over time, thermal and/or mechanical stresses may cause micro-cracks to develop in the resin filler material. Stresses may arise because of strong occlusal (chewing and clenching) forces, thermal changes, and digestive enzymes, all of which may cause cracking, abrasion, tension, and weakening of the resin filler materials. If not repaired, the micro-cracks may propagate with corresponding catastrophic failure of the resin filler material. However, micro-cracks are difficult to detect, and even if detected, may not be repairable in situ using current methods and materials. Instead, repair may require complete removal of the resin filler material.

SUMMARY

Dental composites as disclosed herein are made more durable and with increased longevity by giving them self-healing capabilities. The self-healing may be triggered automatically as a result of micro-cracking, induced by thereto/ mechanical fatigue. Self-healing dental composites may intrinsically repair the micro-crack and prevent the crack from propagating to catastrophic failure, thus significantly extending the service life of the dental composite. During the self-healing process, antibacterial agents may be released to provide protection of the composites against cariogenic bacteria. The herein disclosed self-healing dental composites also may improve the remineralization of tooth and caries prevention though fluoride release.

Common components of dental composites typically comprise monomers (or a polymer matrix), glass fillers, coupling agents to enhance bonding between the polymer matrix and glass fillers, initiators, and other additives including inhibitors and pigment.

In an embodiment, a multi-functional self-healing dental composite includes two extra components in addition to the common components: a plurality of healing powder sites distributed throughout the polymer matrix and healing-liquid containing micro-capsules distributed throughout the polymer matrix.

In this embodiment, each of the micro-capsules has an encapsulation shell formed by the reaction of tetraethyl orthosilicate (TEOS) in acid in the presence of the healing liquid. The healing liquid may be an aqueous solution of homopolymer or copolymer of carboxylic acid, typically polyacrylic acid (PAA) with added reaction-controlling additives, typically tartaric acid. The healing powder may be an acid-soluble glass with a higher alumina-silicate ratio than common glass, i.e., calcium fluoroaluminosilicate glass, to increases its reactivity with healing liquid. The healing liquid reacts with the healing powder and forms a glass ionomer cement (GIC), which is a dental restorative material that is based on the reaction of silicate glass powder and polyalkenoic acid, and which would have been applied directly to restore eroded areas on teeth.

The multi-functional self-healing dental composites (SHDC) provide automatic and autonomous repair of micro-cracks. When a micro-crack ruptures a micro-capsule, the healing liquid is released, and dissolves and reacts with the healing powder to form the glass ionomer cement, thus filling the fractures, discontinuities, fissures, or other minor imperfections that might otherwise expand and propagate, and eventually degrade the mechanical and structural integrity of the dental composites.

The SHDCs may be made of materials that have been clinically tested and approved to be physiologically safe in human as restorative materials; thus the SHDCs can be adapted in clinical use readily.

The SHDCs may provide protection for the composites against cariogenic bacteria. In an embodiment, one or more of the micro-capsules containing a healing liquid also may contain antibacterial agents in an aqueous solution; for example, chlorhexidine may be used as the antibacterial agent, and will be released with the healing liquid to provide simultaneous protection against harmful bacteria and micro-organisms.

The SHDCs may prevent secondary caries through fluoride release. The healing powder and the cement formed after healing may release fluoride over a long period, which provides a practical approach to prevent secondary caries.

The SHDCs may enhance remineralizaiton of teeth. Calcium phosphate particles including amorphous calcium phosphate and hydroxyapatite may be added to the healing powder as mineral sources. The calcium phosphate particles may react with the healing liquid and release ions that are needed for tooth remineralization.

Among the advantages of the disclosed multifunctional SHDCs are applying clinically proven GIC chemistry that forms cements, instead of polymers, to fill the fractures, discontinuities, fissures, or other minor imperfections that might otherwise expand and propagate, and eventually degrade the mechanical and structural integrity of the dental composites. Due to the chemical and physical nature of glass ionomer cements, the disclosed multi-functional SHDCs provide clinically proven and non-toxic components, greater resistance to fracturing, and better durability and toughness, as compared to traditional composites. Additional advantages of using glass ionomer cements include good adhesion to teeth and fluoride release are impossible to be achieved through the monomer/catalyst approaches.

Another embodiment of the SHDCs includes robust encapsulation and delivery of the healing liquid, which determines the GIC forming reaction time and the strength of the SHDCs. The healing liquid may be protected by silica micro-capsules and delivered when the capsules are broken by cracking. The healing liquid has a low viscosity and a long shelf life, so that the healing liquid can be delivered when needed. Encapsulation of the healing liquid may be achieved using a sol-gel process of tetraethoxysilane (TEOS) in a water/oil (W/O) emulsion with the healing liquid, a nonionic surfactant, and an organic solvent (e.g., hexane). This protocol delivers chemically inert, free flowing/non-sintered silica micro-capsules of uniform size, maximum cavity space for encapsulated healing liquid, optimal wall thickness and mechanical strength.

The healing efficiency/capability of the multi-functional self-healing dental composites may be enhanced through one or multiple modifications of the micro-capsules, healing powder and healing liquid which will optimize formation of glass ionomer cement and ensure that the micro-cracks reach and rupture the micro-capsules and release sufficient amount of healing liquid.

In this embodiment, the strength of the micro-capsules and the fill fraction of the healing liquid within may be adjusted through the size of micro-capsules and wall thickness of micro-capsules to provide the maximum possible fill fraction of healing liquid. The fill fraction of the healing liquid in the micro-capsule is expected to vary between 30 weight percent (wt %) and 80 wt %; the rupture of the micro-capsules may be controlled by varying wall-thickness and size of the micro-capsules and/or applying surface treatments to the micro-capsules, e.g., salinization of the micro-capsules. The GIC forming reaction time affects healing efficiency; if the cement forming reaction time is too short or too long, the healing efficiency will be impaired. The cement forming reaction time may be adjusted by varying the molecular weight and concentration of the carboxylic acid polymers, cross-links, and amount of additives, e.g., tartaric acid, in the healing liquid. The cement forming time also may be adjusted by varying the size and composition of healing powder. For example, mixing solid polyacrylic acid with the healing powder will shorten the cement forming reaction time. Usage of above modifications to enhance healing efficiency/capability of the multi-functional SHDCs needs to consider the overall performance of the composites and their application. For example, high healing efficiency may not necessarily be the best option considering the application and overall performance of the composites.

In an embodiment, the multi-functional SHDC includes a dental resin monomer or a combination of dental resin monomers; a polymerization initiator; a glass filler; a plurality of healing-liquid containing micro-capsules distributed throughout the monomer, each of the micro-capsules comprising a healing liquid. The healing liquid comprises polymer(s) of carboxylic acid(s), such as homo polymer of acrylic acid or copolymer of acrylic acid and itaconic acid, and reaction controlling additives. The SHDC further includes a plurality of healing powder particles approximately evenly distributed throughout the matrix. Healing powder particles comprises alumina and silica and one or more elements such as calcium, fluoride, strontium, lanthanum, phosphate, sodium, potassium, barium, titanium, zinc, and zirconium.

The monomer(s) of the SHDC may comprise monomers selected from the group consisting of monomers) containing one or more methacrylate group(s), including 2,2-bis[4-(2-hydroxy-3-methacryloyloxypropoxy)phenyl]propane (Bis-GMA), dimethacryloxyethyl 2,2,4-trimethylhexamethylene diurethane (UDMA), 1,6-bis-[2-methacryloxy-ethoxycarbo-nylamino]-2,2,4-trimethylhexane (UEDMA), triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DEGDMA), hexanediol dimethacrylate (HDMA), hexanediol diacrylate (HDDA), trimethylolpropanetriacrylate (TMPTA), Hydroxyethyl methacrylate (HEMA), trimethylolpropanetrimethacrylate (TMPTMA), ethoxylated-trimethylol-propane-tri-acrylate (EOTMPTA), ethoxylated bisphenol A dimethacrylate (EB-PADMA); monomer(s) containing one or more acrylate group(s); monomer(s) containing one or more cyanoacrylate group(s), including methyl 2-cyanoacrylate, ethyl-2-cyano-acrylate, n-butyl-cyanoacrylate and 2-octyl cyanoacrylate; monomer(s) containing one or more vinylbenzyl group(s); monomer(s) polymerizable through ring-opening reaction; and monomer(s) polymerizable through dehydration synthesis and form ester, urethane or amide groups.

DESCRIPTION OF THE DRAWINGS

The detailed description refers to the following drawings in which.

DETAILED DESCRIPTION

Figure 1A:
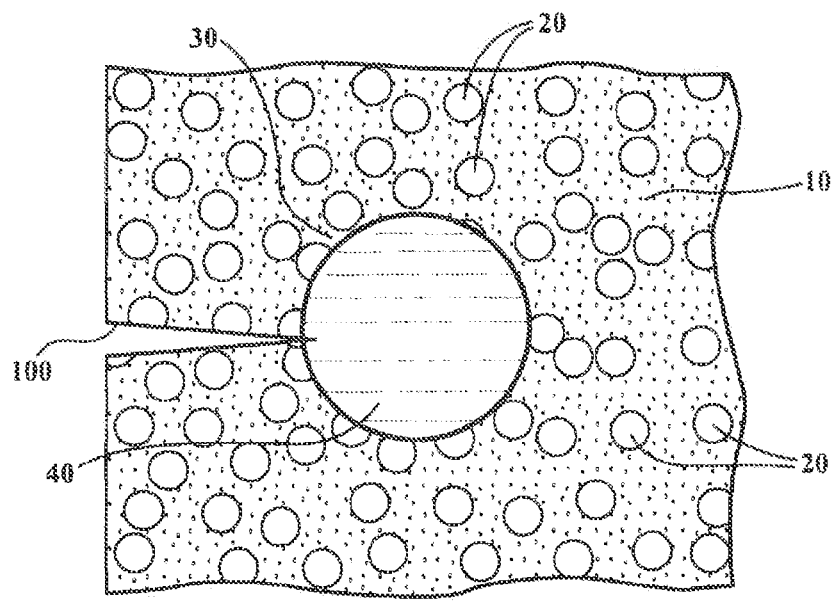
FIGS. 1A-1C illustrate, conceptually, an exemplary self-healing dental composite and a corresponding self-healing process.

Composites used in dental applications, such as resin filler materials for cavities, are susceptible to micro-cracking brought on by thermal and mechanical stresses resulting from strong occlusal (chewing and clenching) forces, and thermal changes, all of which may weaken the resin filler materials. If not repaired, the micro cracks may propagate with corresponding catastrophic failure of the filler materials. However, micro-cracks are difficult to detect, and even if detected, cannot be repaired in situ using current methods and materials; instead, repair usually requires complete replacement of the resin filler material.

One solution to micro-cracking and other fractures of current dental composites is proposed in Goss et al., U.S. Pat. No. 8,735,463. Goss discloses dental composites that incorporate a self-healing mechanism that includes microspheres encapsulating a monomer. When a fracture occurs, a microsphere ruptures and the monomer is released into the fracture. The monomer then is polymerized by a polymerization initiator or other catalyst present in the dental composite. Goss' microspheres make up from 2.5 wt % to 14 wt % of the dental composite. The shells of the microspheres are themselves a polymer. Such shell material does not have the structural strength ideal for long-term dental restorative applications. For example, the use of polymer shell material lowers the elastic modulus of the dental composite relative to that provided by the herein disclosed micro-capsules. In addition, Goss' monomers and catalysts contain toxic chemicals and are a potential threat to human health.

To overcome the limitations of current resin filler materials, disclosed herein are multi-functional self-healing dental composites (SHDCs) containing repair components that automatically and autonomously restore micro-cracks or reduce crack propagation, thereby significantly extending the service life of the SHDCs without the need for external repair or any other human intervention. In addition, the SHDCs may release water soluble antibacterial agents during healing, enhance tooth remineralization, and prevent secondary caries through fluoride release. Also disclosed are methods for making and using the SHDCs.

The SHDC may include components in traditional composites, such as a monomer or a combination of monomers (or a polymer matrix), glass fillers, coupling agents, initiators, and other additives including inhibitors and pigment. In addition, the SHDCs also contain two new components: healing powder and healing liquid encapsulated in silica microcapsules Monomers are molecules that can be bonded together through covalent bonds to form a polymer matrix, a resin network, a resin, or a polymer. Glass filler with various size and shape particles may be added to achieve suitable physical and mechanical performance of the composites in oral environments; for example, increasing of elastic modulus and toughness, and reducing polymerization shrinkage. Coupling agents enhance the bonding between the polymer matrix and the glass fillers. Initiators may be used to start the reaction converting the monomers into polymers. Additives including inhibitors and pigment may be used to adjust the shelf-life of the composite and for cosmetic purposes, respectively.

In an embodiment, the SHDCs combine a biocompatible liquid encapsulation technology and a suitable dental cement technology. The dental cement may have two components: a healing liquid and a healing powder. The healing liquid is retained in micro-capsules distributed throughout the dental composite. When triggered, the micro-capsules rupture, allowing mixing and reacting of the healing liquid and healing powder to form the dental cement. In a more specific embodiment, the dental cement technology is glass ionomer cement (GIC) technology. In this embodiment, micro-capsules distributed approximately homogenously in a dental composite contain a healing liquid such as homo-polymers or copolymers of polycarboxylic acid, typically polyacrylic acid (PAA), and reaction controlling additives, typically tartaric acid, that, when released from the micro-capsules, react with healing powder particles distributed throughout the dental composite to form a reparative GIC within cracks that may occur in the SHDCs. The micro-capsule protects the healing liquid from premature release during resin composite preparation, installation, and use as a filler material, until conditions within the SHDC require self-repair. Such repair, or crack healing, is triggered by a propagating crack that ruptures the embedded micro-capsules, releasing the healing liquid into the crack plane by capillary action.

An example of GIC technology suitable for the herein disclosed SHDCs is described in the literature including "Glass Ionomer Cement Formulation: 1. The Preparation of Novel Fluroaluminosilicate Glasses High in Flourine (healing powder)," to Brian Kent et al., Jun. 1, 1979 and Glass-ionomer Cement Formulation. II. The Synthesis of Novel Polycarboxylic Adds (healing liquid)," to Stephen Crisp et al., Jun. 1, 1980, both of which are available at www.sagepublications.com, and both of which are herein incorporated by reference. New developments in GIC technology may be used in SHOO as well.

In an embodiment of the herein disclosed SHDCs, the healing powder comprises an acid-soluble glass with a higher alumina-silicate ratio than common glass, i.e., calcium fluoroaluminosilicate glass, to increase its reactivity with the healing liquid. The healing liquid comprises an aqueous solution of polycarboxylic acid, such as PAA, with added tartaric acid to optimize viscosity and setting time (acid-base reaction between the PAA and the glass with concomitant release of $Ca^{2+}$, $Al^{3+}$ and $F^-$). The presence of calcium and fluoride creates an ideal balance between reactivity and stability. The resulting fully set GIC comprises a composite of glass particles surrounded by silica gel in a matrix of polyanions cross-linked by ionic bridges. Water serves as the reaction medium initially; it also hydrates the cross-linked agents and yields a stable gel structure strong enough to prevent excessive water penetration and/or contamination.

The great flexibility and clinical efficacy of GICs justify their utilization in the SHDCs. The GICs are biocompatible, inherently adhere to tooth structure, exhibit little or no shrinkage (good marginal healing) and release $F^-$ to prevent/inhibit caries.

Multiple functionality of the novel SHDCs may be achieved by encapsulating the active component in the micro-capsules or by mixing with healing powder. Water-based antimicrobial agents such as chlorhexidine (used in mouthwashes to reduce dental plaque and oral bacteria) may be incorporated into micro-capsules with healing liquid and provide instant protection against bacterial attack that is not achievable otherwise.

The SHDCs may be used as a dental restorative material; specifically, the SHDCs may be used as filing materials to restore tooth cavities. The multi-functional self-healing dental composites also may be equally applicable and appropriate, for example, as composites used in other types of reparative, reconstructive, protective, or palliative procedures, such as such as implants, onlays, veneers, dentures, cores and buildups, root canal posts, mouthpieces, orthodontic brackets, crowns, bridges, cements for single or multiple tooth prostheses, permanent and provisional restorations, or other types of material that may be placed by a dentist or fabricated in a dental laboratory. The resin composites further may be used to provide drug delivery within teeth, especially at the restoration/tooth interface.

Figure 1B:
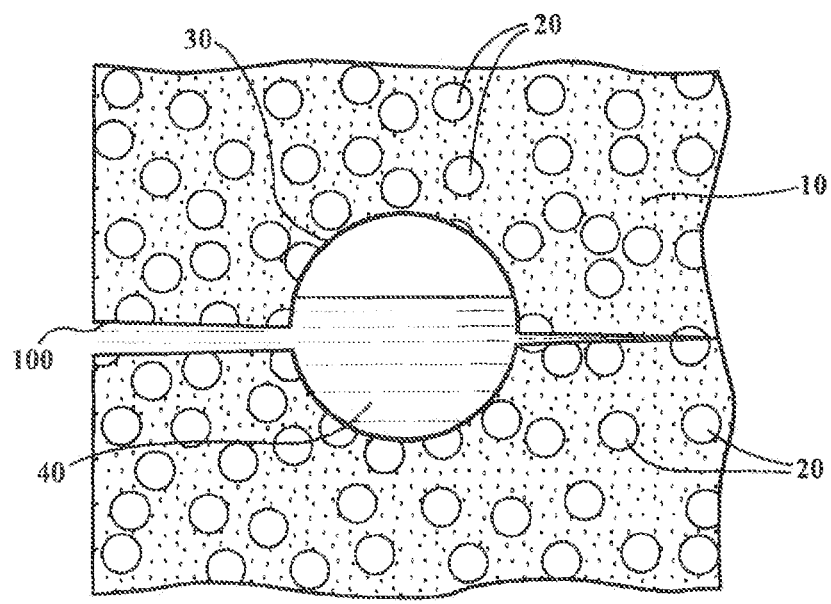
Figure 1C:
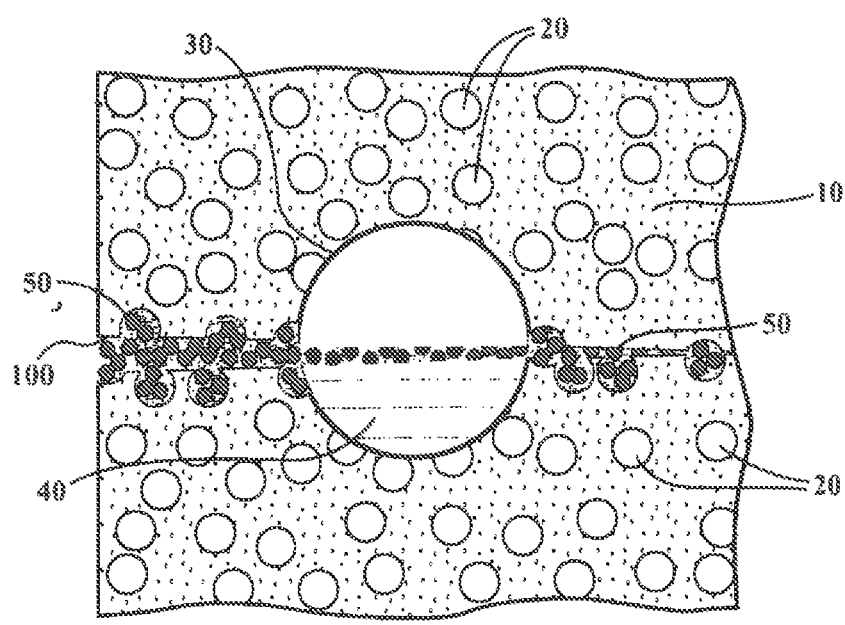

FIGS. 1A-1C illustrate embodiments of self-healing using the herein disclosed SHDCs. FIG. 1A illustrates SHDC 10 in which are distributed healing powders 20 and micro-capsules 30 containing healing liquid 40. As noted, the healing powders 20 may be aluminosilicate powder and the healing liquid may be an acid that reacts with the healing powder, such as a polymer of acrylic acid. Also shown in FIG. 1A is crack 100, which is forming and beginning to propagate through the SHDC 10.

In FIG. 1B, the crack 100 has propagated further into the SHDC 10, causing micro-capsules 30 in the path of the crack 100 to break and releasing the healing liquid 40 through capillary action.

In FIG. 1C, the healing liquid 40 is shown to dissolve and react with the healing powder 20 to form GIC 50, which heals the crack 100. As illustrated in FIG. 1C, enough healing liquid 40 has been released from the ruptured micro-capsules 30 to fill the propagating crack 100 by reacting with the healing powder 20 located in the vicinity of the propagating crack 100. As also illustrated, some healing liquid 40 may remain in the micro-capsules 30, depending on the size of the crack 100.

The healing liquid-containing micro-capsules 30 and the healing powder 20 may be provided for dental applications carried in a suitable dental resin monomer. Once in place in an oral cavity, the monomer is light cured to form a hardened solid dental composite, with the healing powder and micro-capsules approximately evenly, or homogenously, distributed throughout the composite.

The SHDC 10 is designed to automatically and autonomously repair micro-cracks that are hard to detect and almost impossible to repair by current dental composite repair methods. As noted herein, micro-cracking induced by thermal and mechanical fatigue is a long-standing problem in dental composites. Continuous micro-cracking deterioration may lead to catastrophic failure of dental restorations such as filings and hence may shorten the duration that a filling protects a tooth. The herein disclosed SHDCs intrinsically correct minor damage caused by routine activities, such as chewing and grinding, as well as the presence of digestive enzymes, in the oral cavity. The SHDCs may significantly increase service life of dental restoratives and may save patients time and money by eliminating extra visits to a dental office to repair/replace cracked restorations and the additional expenses incurred.

The healing liquid 40 is protected by encapsulation in the micro-capsules 30, which provide necessary mechanical properties needed for dental composites. Rather than polyurethane as an encapsulation material (which will significantly reduce elastic modulus when used in dental composites), the micro-capsules 30 employ materials selected for theft biocompatibility and mechanical performance, such that they are strong enough not to rupture prematurely, do not adversely affect the mechanical strength of the dental composite, and do not cause harmful effects on the human body. In another embodiment, beneficial chemicals can be incorporated within the micro-capsules to aid the body when released upon breaking the micro-capsules, provided that the encapsulation material is chemically compatible with the agent to be released and the release can be controlled.

In an embodiment, the liquid-containing micro-capsules 30 are made in a water/oil emulsion. The she of the micro-capsule 30 is formed by the reaction of tetraethyl orthosilicate (TEOS) and an aqueous solution of the healing liquid, effectively trapping the healing liquid within a layer of silica. The micro-capsules then are separated from the mixture, washed, dried and salinized as necessary. Next, the micro-capsules 30 are mixed into a composite containing filler silica, the healing powder (which also primarily is comprised of silica, but also may contain calcium salts, alumina and fluoride ions), and dental resin monomers (e.g., Bis-GMA/HEMA). The result is a dental composite with an approximately homogenous distribution of micro-capsules and healing powder that may be used in a variety of dental applications. Once placed in an oral environment (a patient's mouth), the composite is cured or polymerized to form a hardened solid where all components are approximately evenly distributed within the cured composite. The curing or polymerization may be effected using one of heat, ultraviolet light, visible light, free radical polymerization, cationic polymerization, and anionic polymerization Forming the micro-capsules may require consideration of the specific application of the dental SHDC from chemical, bio compatibility, and mechanical perspectives. For example, increasing the concentration of healing liquid should lead to a reduced setting time for the cement reaction, and thus improve the healing process. However, because of the TEOS/water emulsion used to form the micro-capsules, a significant amount of water may be needed to develop droplets of suitable size, which in turn forms the micro-capsules. A polycarboxylic acid concentration in healing liquid of higher than 5 wt % has been found to allow a fast cement setting time yet contain enough water to form the micro-capsules. The herein-disclosed SHDCs may comprise micro-capsules having a 10 wt % or higher concentration of poly carboxylic acid.

Fracture toughness of the micro-capsules presents another challenge. If the encapsulation shells are too thick, some micro-capsules along the propagation line of the crack may not fracture, and thus enough liquid may not be available to close the crack. Surface treatment of the micro-capsules, such as salinization, may be used to increase the number of micro-capsules that rupture.

In addition to encapsulation of the healing liquid, other materials, including, for example, water soluble antibacterial agents, may be encapsulated within the same shell as the healing liquid. In this embodiment, when the micro-capsule ruptures, the antibacterial agent is released into the propagating crack.

In another embodiment of the SHDCs, a portion of healing powder may be replaced with hydroxyapatite (HAP), fluorapatite, or amorphous calcium phosphate (ACP) to achieve tooth remineralization. The calcium phosphate particles may react with healing liquid and release ions that needed for remineralization of tooth.

In various embodiments, the healing efficiency/capability of the multi-functional self-healing dental composites is enhanced through one or multiple modifications of the micro-capsules, healing powder and healing liquid which will optimize formation of glass ionomer cement and ensure that the micro-cracks reach and rupture the micro-capsules and release sufficient amount of healing liquid.

In an embodiment, the strength of the micro-capsules and the fill fraction of the healing liquid within may be adjusted through their wall thickness by varying the ratio of healing liquid to TEOS to provide the maximum practical fill fraction of healing liquid. The fill fraction of the healing liquid in the micro-capsule is expected to vary between 30 wt % and 80 wt % depending on the micro-capsule size and well thickness; the rupture of the micro-capsules may be directed through varying wall-thickness and size of the micro-capsules and/or applying a surface treatment such as salinization to the micro-capsules. The GIC forming reaction time is important in adjusting healing efficiency. If the reaction forming time is too slow, the healing efficiency may be impaired. The GIC forming reaction time may be adjusted by varying the molecular weight and concentration of PAA, cross-links, and amount of additives, such as tartaric acid, in the healing liquid. The GIC forming reaction time also may be controlled by varying size and composition of healing powder. For example, mixing solid PAA with healing powder will shorten the GIC forming reaction time. The usage of above modifications to enhance healing efficiency/capability of the multi-functional SHDCs needs to consider the overall performance of the composites and their application. High healing efficiency may not be necessarily the best option considering the application and overall performance of the composites.

The SHDCs disclosed herein were characterized based on the following mechanical, morphological and chemical evaluations.

Elastic modulus of the micro-capsules was determined according to ISO4049: 2009. Five bars (2 mm×2 mm×25 mm) of each composition were made following the SHDC construction method descripted above. Elastic modulus was measured using a Dynamic Mechanical Analysis (DMA Q800, TA Instruments, DE, USA) set with a loading rate of 1 N/min. The specimens were placed on a 3-point bending test device, which was constructed with 20 mm span distance between supports and ensuring an equally distributed load. The elastic modulus of each material was calculated according to ISO4049: 2009.

Mechanical evaluation was carried out through fracture toughness, which was determined according to ISO6872: 2014. Five bars (25 mm×4 mm×3 mm) of each composition were made following the SHDC construction method descripted above. The specimens were notched by sawing with an IsoMet Low Speed Saw (Buehler, Lake Bluff, Ill., USA) fitted with NTI Rex Diamond Discs (NTI-Kahla GmbH, Kahla, Germany), and the notch was sharpened using a razor blade polished with 3 μm diamond paste. Fracture toughness was assessed using an Instron 5500R Universal Testing Machine (Instron Corp., Canton, Mass., USA) set with a loading speed of 0.5 mm/min. The specimens were placed on a 3-point bending test device, which was constructed with 20 mm span distance between supports and ensuring an equally distributed load. Each specimen was loaded until critically fractured, and the load was immediately stopped to recover the specimen. A drop of water was added into the notch of the specimen, and the specimen was rested for 4 days. The process was then repeated to measure the peak bad of the healed specimen. A Helios NanoLab 650 Dual Beam SEM/FIB (FEI Company, Hillsboro, Oreg., USA) with an X-Max 80 mm² SDD-EDS detector (Oxford Instruments, Abingdon, Oxfordshire, UK) was used to analyze the elemental composition of the fractured and healed surfaces.

The fracture toughness was obtained using a single edge V-notched beam (SEVNB) method based on the peak load to fracture the specimens. The SEVNB method induced a controlled cracking in the specimen and, if the load on the specimen was precisely stopped, can critically fracture the specimen without severing it into two pieces. At this state, the specimen was significantly damaged internally, but still remained attached to each other. The initial fracture toughness ($K_{IC}^{ini}$) was then calculated according to Equation 1. Water was added into the notch, and the specimen was rested for 4 days. The specimen was fractured again using the same method, and the new fracture toughness ($K_{IC}^{heal}$) was calculated. The healing efficiency is defined as the percentage of the new fracture toughness recovered in comparison with the original fracture toughness ($K_{IC}^{heal}/K_{IC}^{ini}*100\%$). A set of non-healing composites with the same mass percentage of water-filled micro-capsules were used as the controls.

$$K_{Ic} = g\left[\frac{F_{max}S_0 \times 10^{-6}}{BW^{1.5}}\right]\left[\frac{3(a/W)^{1.5}}{2(1-a/W)^{1.5}}\right].$$ Equation 1

The equation for calculating fracture toughness $K_{IC}$ using a three-point fixture, where $S_0$=span, W=thickness, B=width, a=notch depth, $F_{max}$=fracture load, and g=$A_0$+$A_1$(a/W)+$A_2$(a/W)$^2$+$A_3$(a/W)$^3$+$A_4$(a/W)$^4$+$A_5$(a/W)$^5$. The coefficients to calculate the polynomial g when $S_0$/W=5 are: $A_0$=1.9109, $A_1$=−5.1552, $A_2$=12.6880, $A_3$=−19.5736, $A_4$=15.9377, $A_5$=−5.1454

EXAMPLES

Example 1: Making of Micro-Capsules Containing Polyacrylic Acid

SPAN 80 (4.00 g) was added to a mixture of decahydronaphthalene (100 mL) and de-ionized water (4.00 g), and stirred at 400 RPM. A polyacrylic acid solution (4.0 mL) was added drop-wise and the mixture was continuous stirred for 1 h. TEOS (4.0 mL) was activated with hydrochloric acid (2M, 1.0 mL) and stirred for 1 h. The activated TEOS was then added into the decahydronaphthalene/water mixture and stirred at 400 RPM for 1 h. The mixture was heated to 60° C. for 45 minutes. A white precipitate was collected from the mixture and washed with ethanol to give healing liquid-containing micro-capsules.

Example 2: Silanization of Micro-Capsules with Methacrylate-Functionalized Silane 3-methacryloxypropyltrimethoxy silane (0.2 mL) was added to hexane (20 mL). Formic acid (88%, 0.020 mL) was added as a catalyst. The healing liquid-containing micro-capsules were mixed in this solution and stirred for 5 minutes. The micro-capsules were collected by filtration, washed with hexane (20 and ethanol (20 mL) then dried under vacuum.

Example 3: Making of Micro-Capsules Containing Polymer Acrylic Acid and Fluoride Salt SPAN 80 (4.00 g) was added to a mixture of decahydronaphthalene (100 mL) and sodium fluoride solution (4.00 g, 0.00012 wt %), and stirred at 400 RPM. An aqueous solution of polyacrylic acid (4.0 mL) was added drop-wise and the mixture was continuous stirred for 1 h. TEOS (4.0 mL) was activated with hydrochloric acid (2M, 1.0 mL) and stirred for 1 h. The activated TEOS was then added into the decahydronaphthalene/water mixture and stirred at 400 RPM for 1 h. The mixture was heated to 60° C. for 45 minutes. A white precipitate was collected from the mixture and washed with ethanol to give fluoride ions and healing liquid-containing micro-capsules.

Example 4: Making of Micro-Capsules Containing Polyacrylic Acid and Chlorhexidine Acetate SPAN 80 (4.00 g) was added to a mixture of decahydronaphthalene (100 mL) and chlorhexidine acetate solution (4.00 g, 0.05 wt %), and stirred at 400 RPM. A solution of polyacrylic acid (4.0 mL) was added drop-wise and the mixture was continuous stirred for 1 h. TEOS (4.0 mL) was activated with hydrochloric acid (2M, 1.0 mL) and stirred for 1 h. The activated TEOS was then added into the decahydronaphthalene/water mixture and stirred at 400 RPM for 1 h. The mixture was heated to 60° C. for 45 minutes. A white precipitate was collected from the mixture and washed with ethanol to give chlorohexidine and healing liquid-containing micro-capsules.

Example 5: Making of Self-Healing Dental Composites (SHDC)

The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt % total): strontium glass fillers (70 wt %) and silanized healing liquid-containing micro-capsules (5 wt %). A control composite was made with 5 wt % of water-containing micro-capsules.

Example 6: Mechanical, and Chemical Evaluation of Self-Healing Dental Composites The elastic modulus of the self-healing dental composite in example 5 was 10.2±0.7 GPa and the control has the same elastic modulus. The initial fracture toughness ($K_{IC}^{ini}$) was 0.91±0.04 MPa·m$^{1/2}$, and the control had the same $K_{IC}^{ini}$. The self-healing dental composites showed autonomous healing with a healing efficiency at 24.2±3.8%, while the control did not heal. The $K_{IC}^{ini}$ of SHDCs and the controls was the same when the same mass percentage of micro-capsules was used. The $K_{IC}^{ini}$ did not change when up to 5 wt % of micro-capsules were added. Further increase of the micro-capsule loading decreased the $K_{IC}^{ini}$. The $K_{IC}^{ini}$ of SHDCs with 10 wt % of micro-capsules were lower than that of the other compositions. Elemental analysis by EDS indicated that the material formed at the healed cracks had an aluminum-silica-strontium ratio close to that of glass ionomer cement.

Example 7: Making of Self-Healing Dental Composites-Composition 2

The resin mixture was made by combining Bis-GMA and HEMA resin in a 1:1 ratio. Camphoroquinone was added as the photosensitizer at 0.5 wt % and ethyl 4-(dimethylamino)

benzoate at 0.5 wt % was added as the accelerator. The resin, photosensitizer and inhibitor were mixed together. Upon homogenization, this resin blend was mixed with the following fillers (75 wt %): strongtium glass fillers (35 wt %), Ox50 silica nanofillers (5 wt %), polyacrylic acid-containing healing powder (30 wt %) and silanized healing liquid-containing micro-capsules (5 wt %).

Example 8: Making of Self-Healing Dental Composites-Composition 3

A composition for a self-healing dental composite is described as follows. The resin mixture was made by combining Bis-GMA and HEMA resin in a 1:1 ratio. Camphoroquinone was added as the photosensitizer at 0.5 wt % and ethyl 4-(dimethylamino)benzoate at 0.5 wt % was added as the accelerator. The resin, photosensitizer and inhibitor were mixed together. Upon homogenization, this resin blend was mixed with the following fillers (75 wt %): polyacrylic acid-containing healing powder (70 wt %) and silanized healing liquid-containing micro-capsules (5 wt %).

Example 9: Making of Self-Healing Dental Composites-Composition 4

The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt %): healing powder (70 wt %) and silanized healing liquid-containing micro-capsules (5 wt %).

Example 10: Making of Self-Healing Dental Composites-Composition with Fluoride in Micro-Capsules The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin bend was mixed with the following fillers (75 wt %): strontium glass fillers (15 wt %), Ox50 silica nanofillers (5 wt %), healing powder (50 wt %) and silanized healing liquid/fluoride-containing micro-capsules (5 wt %).

Example 11: Making of Self-Healing Dental Composites-Composition with Chlorohexidine in Micro-Capsules for Antimicrobial Purposes The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt %): strontium glass fillers (15 wt), Ox50 silica nanofillers (5 wt %), healing powder (50 wt %) and silanized healing liquid/chlorohexidine-containing micro-capsules (5 wt %).

Example 12: Making of Self-Healing Dental Composites-Composition with Fluoride in Fillers The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt %): healing powder (68 wt %), sodium fluoride (2 wt %), and silanized healing liquid-containing micro-capsules (5 wt %).

Example 13: Making of Self-Healing Dental Composites with Hydroxylapatite

The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt %): healing powder (60 wt %), hydroxyapatite (10 wt %), and silanized healing liquid-containing micro-capsules (5 wt %).

Example 14: Making of Self-Healing Dental Composites with Fluoride and Hydroxyapatite The resin mixture was made by combining Bis-GMA and HEMA resin in a 1:1 ratio. Camphoroquinone was added as the photosensitizer at 0.5 wt % and ethyl 4-(dimethylamino) benzoate at 0.5 wt % was added as the accelerator. The resin, photosensitizer and inhibitor were mixed together. Upon homogenization, this resin blend was mixed with the following fillers (75 wt %): healing powder (58 wt %), sodium fluoride (2 wt %), hydroxyapatite (10 wt %) and silanized healing liquid-containing micro-capsules (5 wt %).

Example 15

A composition of healing powder: calcium aluminosilicate glass ($SiO_2$—29%, $Al_2O_3$—16.6%, $CaF_2$—34.4%, $Na_3AlF_6$—5%, $AlF_3$—5.3%, $AlPO_4$—9.8%).

Example 16

A composition of healing liquid: polyacrylic acid/itaconic acid copolymer (MW=10000) with 5% D(+) tartaric acid.

I claim:
1. A composition of self-healing dental composite, comprising:
   a dental resin monomer or a combination of dental resin monomers;
   a polymerization initiator(s);
   a glass filler(s);
   a plurality of healing-liquid containing micro-capsules distributed throughout the composite, wherein the healing liquid comprises:
      water,
      polycarboxylic acid(s), wherein the polycarboxylic acid(s) comprises a mixture of homo-polymer(s) of acrylic acid, and/or copolymer(s) of acylic acid and itaconic acid, and/or polycarboxylic acid(s) that is used for making glass ionomer cement; and
      reaction controlling additives, wherein the reaction controlling additives comprise small molecule acid(s), including tartaric acid, and
   a plurality of healing powder particles distributed throughout the composite.

2. The self-healing dental composite of claim 1, wherein the dental resin monomer or the combination of dental resin monomers comprise:
monomers selected from the group consisting of monomer(s) containing one or more methacrylate group(s), including 2,2-bis[4-(2-hydroxy-3-methacryloyloxy-propoxy) phenyl]propane (Bis-GMA), dimethacryloxyethyl 2,2,4-trimethylhexamethylene diurethane (UDMA), 1,6-bis-[2-methacryloxy-ethoxycarbonylamino]-2,2,4-trimethylhexane (UEDMA), triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DE-GDMA), hexanediol dimethacrylate (HDMA), hexanediol diacrylate (HDDA), trimethylolpropanetriacrylate (TMPTA), Hydroxyethyl methacrylate (HEMA), trimethylolpropanetrimethacrylate (TMPTMA), ethoxylated-trimethylol-propane-tri-acrylate (EOTMPTA), ethoxylated bisphenol A dimethacrylate (EBPADMA); monomer(s) containing one or more acrylate group(s);
monomer(s) containing one or more cyanoacrylate group(s), including methyl 2-cyanoacrylate, ethyl-2-cyanoacrylate, n-butyl-cyanoacrylate and 2-octyl cyanoacrylate;
monomer(s) containing one or more vinylbenzyl group(s);
monomer(s) polymerizable through ring-opening reaction; and
monomer(s) polymerizable through dehydration synthesis and form ester, urethane or amide groups.

3. The self-healing dental composite of claim 1, wherein the healing powder comprising:
alumina and silica, and
one or more elements chosen from the group comprising calcium, fluoride, aluminium, strontium, lanthanum, phosphate, sodium, potassium, barium, titanium, zinc, and zirconium.

4. The self-healing dental composite of claim 1, wherein the micro-capsules comprise silica shells formed by a hydrolysis-condensation of tetraethyl orthosilicate (TEOS) in the presence of an aqueous solution of the healing liquid.

5. The self-healing dental composite of claim 1, wherein the micro-capsules are surface treated with a silane coupling agent; wherein the silane coupling agent contains at least two functional groups, one reacts with silica and the other copolymerizes with the resin monomer(s).

6. The self-healing dental composite of claim 1, wherein the micro-capsules comprise 1 wt %-40 wt % of the composite.

7. The self-healing dental composite of claim 1, wherein the healing powder comprise 5 wt %-80 wt % of the composite.

8. The self-healing dental composite of claim 1, wherein said resin monomers comprise 10 wt %-95 wt % of the composite.

9. A composition of self-healing dental composite made by curing or polymerizing the resin monomer(s) in claim 1 by using one or more of the following methods: heat, ultraviolet light, visible light, free radical polymerization, cationic polymerization, and anionic polymerization.

10. The composition of self-healing dental composite of claim 9 and its cured or polymerized products in any dental applications, including restorative materials, cements for single or multiple tooth prostheses and orthodontic devices, inlays, onlays, cores and buildups, root canal posts, and provisional restorations.

11. The self-healing dental composite of claim 1, further comprising a tooth remineralization material distributed throughout composite; the remineralization material is chosen from a group consisting of hydroxylapatite (HAP), fluorapatite, and amorphous calcium phosphate (ACP).

12. A composition of self-healing dental composite made by curing or polymerizing the resin monomer(s) in claim 11 by using one or more of the following methods: heat, ultraviolet light, visible light, free radical polymerization, cationic polymerization, and anionic polymerization.

13. The composition of self-healing dental composite of claim 12 and its cured or polymerized products in tooth remineralization, bone remineralization, and any dental applications, including restorative materials, cements for single or multiple tooth prostheses and orthodontic devices, inlays, onlays, cores and buildups, root canal posts, and provisional restorations.

14. The self-healing dental composite of claim 1, further comprising a solid form of homo-polymer or copolymer of carboxcylic acid(s), wherein the polymer is coated on the healing powder and/or mixed with healing powder.

15. A composition of self-healing dental composite made by curing or polymerizing the resin monomer(s) in claim 14 by using one or more of the following methods: heat, ultraviolet light, visible light, free radical polymerization, cationic polymerization, and anionic polymerization.

16. The composition of self-healing dental composite of claim 15 and its cured or polymerized products in any dental applications, including restorative materials, cements for single or multiple tooth prostheses and orthodontic devices, inlays, onlays, cores and buildups, root canal posts, and provisional restorations.

17. The self-healing dental composite of claim 1, wherein one or more of the micro-capsules further encapsulate a secondary component that delivers an antibacterial agent; wherein the secondary component comprising water soluble antimicrobial agents and/or fluoride salt.

18. A composition of self-healing dental composite made by curing or polymerizing the resin monomer(s) in claim 17 by using one or more of the following methods: heat, ultraviolet light, visible light, free radical polymerization, cationic polymerization, and anionic polymerization.

19. The composition of self-healing dental composite of claim 18 and its cured or polymerized products for drug delivery, antimicrobial, and caries prevention purposes in any dental applications, including restorative materials, cements for single or multiple tooth prostheses and orthodontic devices, inlays, onlays, cores and buildups, root canal posts, and provisional restorations.

* * * * *

UNITED STATES PATENT AND TRADEMARK OFFICE
CERTIFICATE OF CORRECTION

PATENT NO. : 9,931,281 B2  
APPLICATION NO. : 14/952492  
DATED : April 3, 2018  
INVENTOR(S) : Jirun Sun Page 1 of 1

It is certified that error appears in the above-identified patent and that said Letters Patent is hereby corrected as shown below:

In the Specification

Column 1, Line 13, after the paragraph entitled "RELATED APPLICATIONS," insert the following:
--STATEMENT OF FEDERALLY SPONSORED RESEARCH
This invention was made with government support under grant U01 DE023752 awarded by the National Institutes of Health. The government has certain rights in the invention.--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*